United States Patent
White et al.

(10) Patent No.: US 9,801,692 B2
(45) Date of Patent: Oct. 31, 2017

(54) INSTRUMENT DEPLOYED TISSUE PROTECTOR

(71) Applicant: Biomet Manufacturing, LLC, Warsaw, IN (US)

(72) Inventors: John R. White, Winona Lake, IN (US); Gregory J. Denham, Warsaw, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 477 days.

(21) Appl. No.: 14/454,007

(22) Filed: Aug. 7, 2014

(65) Prior Publication Data
US 2016/0038131 A1    Feb. 11, 2016

(51) Int. Cl.
  *A61B 17/32* (2006.01)
  *A61B 90/00* (2016.01)
  *A61B 17/00* (2006.01)
(52) U.S. Cl.
  CPC ...... *A61B 90/08* (2016.02); *A61B 17/320016* (2013.01); *A61B 2017/00902* (2013.01); *A61B 2090/08021* (2016.02)
(58) Field of Classification Search
  CPC ...... A61B 17/3496; A61B 2090/08021; A61B 90/04; A61B 17/3494; A61B 2017/0212
  USPC .......................... 606/905; 600/209, 203, 206
  See application file for complete search history.

(56) References Cited

U.S. PATENT DOCUMENTS

| | | | | |
|---|---|---|---|---|
| 5,195,507 A | * | 3/1993 | Bilweis | A61B 1/00082 600/204 |
| 5,308,327 A | * | 5/1994 | Heaven | A61B 17/00234 604/103.09 |
| 5,337,736 A | * | 8/1994 | Reddy | A61B 17/0218 128/898 |
| 5,370,650 A | * | 12/1994 | Tovey | A61B 17/0057 128/899 |
| 5,405,360 A | * | 4/1995 | Tovey | A61B 17/00234 606/151 |
| 5,415,666 A | * | 5/1995 | Gourlay | A61B 17/00234 606/139 |
| 5,439,476 A | * | 8/1995 | Frantzides | A61B 17/0218 600/207 |
| 5,735,845 A | * | 4/1998 | Zupkas | A61B 90/04 128/898 |
| 5,865,728 A | * | 2/1999 | Moll | A61B 17/0218 600/204 |
| 5,895,352 A | * | 4/1999 | Kleiner | A61B 17/02 600/206 |
| 5,904,649 A | * | 5/1999 | Andrese | A61B 17/0218 600/204 |
| 6,206,889 B1 | * | 3/2001 | Bennardo | A61B 17/00234 128/DIG. 24 |
| 7,445,598 B2 | * | 11/2008 | Orban, III | A61B 17/0218 600/210 |
| 8,308,638 B2 | * | 11/2012 | Hart | A61B 1/32 600/206 |

(Continued)

*Primary Examiner* — David Bates
(74) *Attorney, Agent, or Firm* — Schwegman Lundberg & Woessner, P.A.

(57) ABSTRACT

A surgical device includes a guiding instrument; a protector comprised of a protective material held in a non-protecting state by the guiding instrument and having a protection state; and an actuator connected to the protector that is configured to advance the protector along the guiding instrument such that the protector is allowed to assume the protection state.

14 Claims, 5 Drawing Sheets

(56) References Cited

U.S. PATENT DOCUMENTS

| | | | | |
|---|---|---|---|---|
| 8,403,837 | B2* | 3/2013 | Okoniewski | A61B 17/0218 600/201 |
| 8,821,507 | B2* | 9/2014 | Axelson, Jr. | A61B 17/00234 606/14 |
| 9,308,008 | B2* | 4/2016 | Duncan | A61B 17/00234 |
| 2005/0228232 | A1* | 10/2005 | Gillinov | A61B 17/02 600/209 |
| 2006/0074277 | A1* | 4/2006 | Yoshida | A61B 17/0218 600/209 |
| 2006/0241648 | A1* | 10/2006 | Bleich | A61B 17/00234 606/103 |
| 2007/0282355 | A1* | 12/2007 | Brown | A61B 17/122 606/151 |
| 2009/0125036 | A1* | 5/2009 | Bleich | A61B 17/1671 606/110 |
| 2009/0156882 | A1* | 6/2009 | Chi Sing | A61N 5/1015 600/7 |
| 2011/0166579 | A1* | 7/2011 | Deem | A61B 17/025 606/90 |
| 2012/0088960 | A1* | 4/2012 | Kubisen | A61B 17/02 600/37 |

* cited by examiner

INSTRUMENT DEPLOYED TISSUE PROTECTOR

BACKGROUND OF THE INVENTION

1. Field of the Invention

The present invention relates to surgical devices, and, more particularly, to orthopaedic surgical devices.

2. Description of the Related Art

Joint arthroscopy is an orthopaedic procedure that is performed to evaluate a joint space and, if necessary, treat disease tissue that is found. Joint arthroscopy is performed with sharp surgical instruments, and treatment of diseased tissue in the joint space often requires removing the diseased tissue with cutting or other damaging procedures. One increasingly common joint arthroscopy procedure is hip arthroscopy, which evaluates and treats the joint between the femur and the acetabulum. The number of hip arthroscopy procedures that are performed annually have rapidly grown over the past five years.

One concern when performing a hip arthroscopy procedure is damaging healthy tissue when visualizing the joint or removing diseased tissue. Direct visualization is not typically used for the procedure, and the surgeon relies on an inserted camera to visualize the joint and guide the instruments during the procedure. As the camera can only visualize what is in its limited line of sight, there is a risk that the sharp instruments used to repair the diseased tissue can be mishandled such that they damage cartilage on the femoral head or the acetabulum.

What is needed in the art is a way to protect healthy tissue during a joint arthroscopy procedure.

SUMMARY OF THE INVENTION

The present invention provides a tissue protector that can be placed on an orthopaedic target or an orthopaedic instrument to protect the orthopaedic target during an arthroscopy procedure.

The invention in one form is directed to a surgical device including a guiding instrument; a protector comprised of a protective material held in a non-protecting state by the guiding instrument and having a protection state; and an actuator connected to the protector that is configured to advance the protector along the guiding instrument such that the protector is allowed to assume the protection state.

The invention in another form is directed to a method for protecting an orthopaedic target including the steps of providing a surgical device that includes a guiding instrument, a protector comprised of a protective material held in a non-protecting state by the guiding instrument and having a protection state, and an actuator connected to the protector that is configured to advance the protector. The surgical device is positioned adjacent to the orthopaedic target. The protector is advanced by the actuator such that the protector assumes the protection state.

The invention in yet another form is directed to a surgical device that includes an orthopaedic instrument having a tissue destructive feature, a guiding instrument connected to the orthopaedic instrument that is configured to allow the orthopaedic instrument to slide along the guiding instrument, and a protector covering the tissue destructive feature and held by the guiding instrument. The protector is configured to be releasably attached to the tissue destructive feature. The protector is configured to slide farther along the guiding instrument than the tissue destructive feature and release from the tissue destructive feature after sliding a farther distance along the guiding instrument than the tissue destructive feature.

An advantage of the present invention is that it provides a minimally invasive way to protect healthy tissue from being damaged during an arthroscopy procedure.

Another advantage is that the protector can include features that assist in performing the arthroscopy procedure.

Yet another advantage is the present invention can be included on an orthopaedic surgical device that will be used during the arthroscopy procedure to protect healthy tissue.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
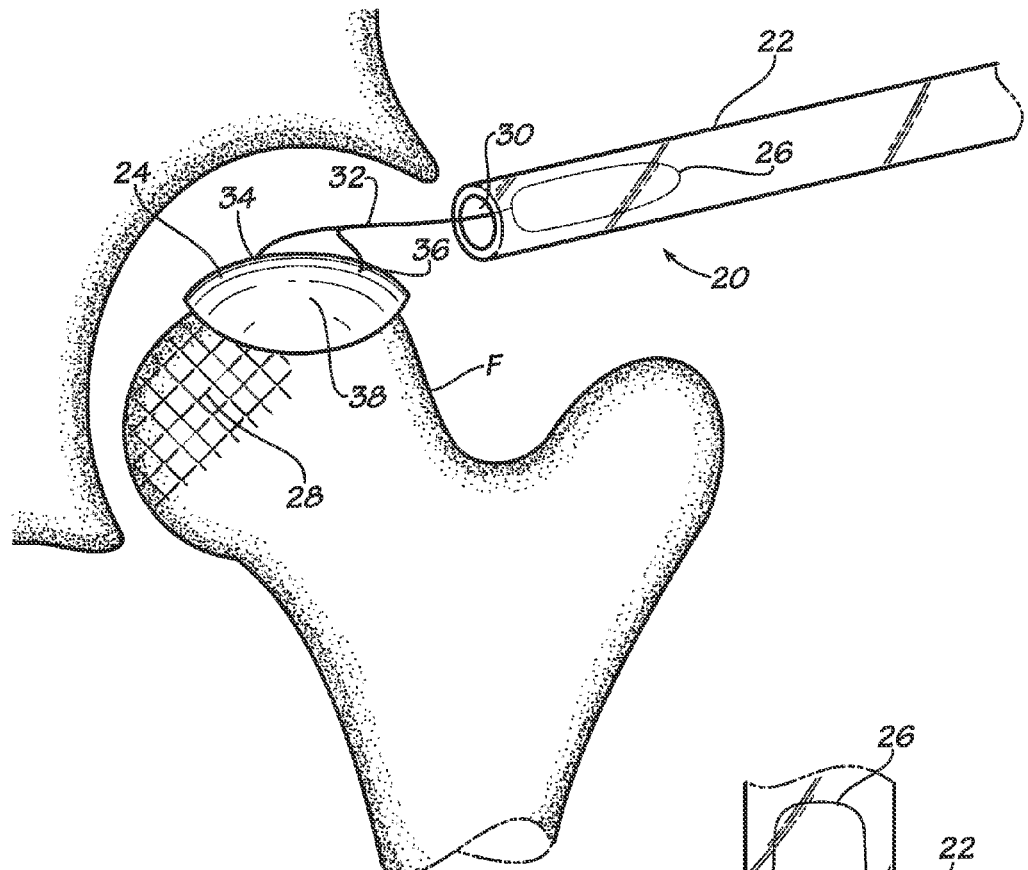
FIG. 1 is a perspective view of an embodiment of the present invention being used to protect healthy tissue on a femur.
Figure 3:
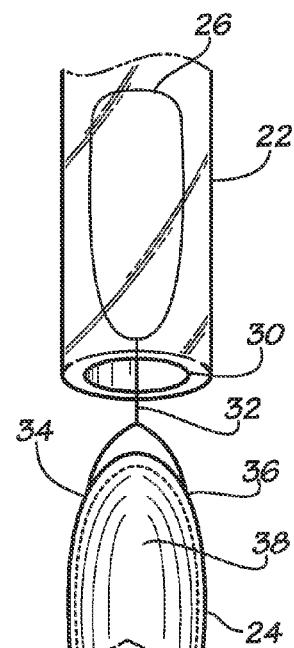
FIG. 3 is a perspective view of the protector cap shown in FIGS. 1 and 2 in a collapsed state.

Referring now to the drawings, and more particularly to FIG. 1, there is shown a surgical device 20 which generally includes a guiding instrument 22, a protector 24 that has a protection state and a non-protecting state held by the guiding instrument 22, and an actuator 26 connected to the protector 24. The guiding instrument 22 shown in FIGS. 1 and 3 is a cannula that is sized to be used in an arthroscopic procedure, in this case a hip arthroscopy. Guiding instruments other than cannulas are contemplated as being used in the present invention, such as introducers and jigs. The guiding instrument 22 can be used exclusively to position and deploy the protector 24 or could also be used with other surgical instruments during the arthroscopy procedure. The guiding instrument 22 can be made of any suitable biocompatible material, including metals such as stainless steel or titanium and various polymers.

Figure 2:
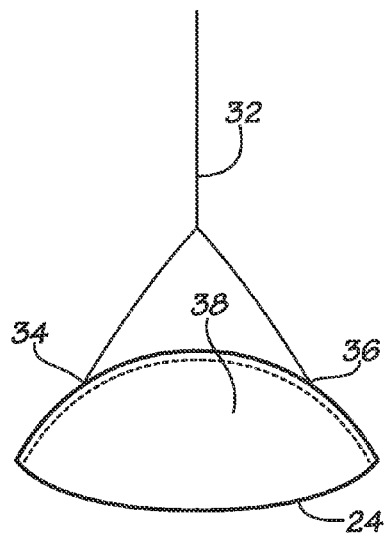
FIG. 2 is a perspective view of the protector cap shown in FIG. 1 in an expanded protection state.

The protector 24, shown in FIGS. 1-12 as a protector cap, can have an expanded protection state and a collapsed non-protecting state. While FIGS. 1-12 show the protector 24, configured as a protector cap, as having an expanded protection state and a collapsed non-protecting state, it is not necessary that the protector be collapsed to be in the non-protecting state or expanded to be in the protection state. Similarly, the protector 24 is shown as a protector cap in FIGS. 1-12, and described as such when referencing FIGS. 1-12, but can be configured in other ways that will be described. When the protector cap 24 is expanded into its expanded protection state, the protector cap 24 is deployed on an anatomical feature F, shown as a femur in FIGS. 1-3, such that it covers healthy cartilage 28. The healthy cartilage 28 is targeted and covered by the protector cap 24 to protect it from being damaged by a surgical instrument that will be used near the healthy cartilage 28, which can be referred to as an orthopaedic target. As used herein, "orthopaedic target" may refer to any anatomical feature that is desired to be protected during an arthroscopy procedure and is associated with the skeletal system of an animal, including bones, cartilage, joints, muscles, tendons, ligaments, etc. Prior to being deployed on the femur F, the protector cap 24 was collapsed within the cannula 22 in a non-protecting state, which can be referred to as a "collapsed state" and is shown in FIG. 3. The protector cap's 24 collapsed state within the cannula 22 allows for the protector cap 24 to be positioned adjacent to the orthopaedic target 28 by the cannula 22 and deployed on to the orthopaedic target 28 by the actuator 26. As used herein, the term "adjacent" means sufficiently close to the orthopaedic target 28 that the protector cap 24 can protect the orthopaedic target 28 from damage caused by a surgical instrument. As shown in FIGS. 1-3, the protector cap 24 has a semi-spherical shape in the expanded protection state, but that shape can be adjusted as desired to cover differently shaped anatomic features. The protector cap 24 is comprised of a protective material that has sufficient toughness to reduce the damage experienced by the orthopaedic target 28 from instruments that can be used in the arthroscopy procedure, such as scalpels, suturing needles, burrs, K-wires, or any sharp instrument. It is useful if the protector cap 24 is comprised of a material that can experience significant deformation and then be returned to its original shape. Example materials that are contemplated as being used include silicone, filled silicone, fiber reinforced silicone, ultra-high molecular weight polyethylene (UHMWPE) fibers, polyester, polypropylene, nylon, two-dimensional carbon layers that are bonded with secondary substrate layers, shape-memory materials, and any thermoplastic polymer. The protector cap 24 should not have relatively large, empty openings formed through, like a stent, as large openings formed through the protector cap 24 could allow the orthopaedic target 28 to be exposed to possible damage or not sufficiently reduce penetration through the protector cap 24 to minimize damage to the orthopaedic target 28. That is not to say the protector cap 24 cannot have openings formed through. If the protector cap 24 is, for example, configured as a fibrous network, there can be small openings between adjacent fibers. In this respect, the fibers will act similarly to chainmail, offering good cutting resistance across the surface of the protector cap 24. Optionally, the protector cap 24 could have larger openings formed through that have a point trapping material associated with the openings, which is described below. The protector cap 24 should also have a material thickness that resists penetration through the protector cap 24 by a sharp or abrasive instrument. The thickness of the material to resist penetration will vary based on the material used. The protector cap 24 should be of a sufficient thickness to reduce damage that a scalpel or abrasive or other sharp instrument can do to the orthopaedic target 28, but it is undesirable for the protector cap 24 to be so thick that it interferes with the arthroscopy procedure being performed. It should therefore be appreciated that the materials, shapes and thicknesses of the protector cap 24 of the present invention can be varied to tailor the protector cap 24 to reduce damage to the orthopaedic target 28 by specific instruments and damaging movements used during an arthroscopy procedure.

An actuator 26 is connected to the protector cap 24. The actuator 26 can be any type of element that can advance the protector cap 24 through an open end 30 of the cannula 22 so that the protector cap 24 is at least partially outside the cannula 22 and can assume the expanded protection state. A simple actuator that can be used would be, for example, a push rod that can advance through the cannula 22. It is contemplated that the protector cap 24 can spontaneously assume the protection state when it is no longer constrained within the cannula 22 or that the actuator 26 is connected to the protector cap 24 in such a way that the movement of the actuator 26 causes the protector cap 24 to expand from its collapsed state into its protection state. The movement of the actuator 26 that advances the protector cap 24 out of the cannula 22 does not need to be the same movement that expands the protector cap 24. For example, the actuator 26 can push the protector cap 24 out of the open end 30 of the cannula 22 and then be twisted to cause expansion of the protector cap 24 into the protection state. Other movement combinations by the actuator 26 to advance and expand the protector cap 24 are also possible, depending on the actuator 26 chosen and the protector cap 24 configuration.

As shown in FIGS. 1-3, a tether 32 can be connected to protector cap 24 and held within the cannula 22. The tether 32 can be a thin, flexible wire or string that connects to the protector cap 24 at two spaced apart connection points 34, 36 on a surface 38 of the protector cap 24. The tether 32 allows for the protector cap 24 to be easily retrieved from the femur F when the arthroscopy procedure is finished. The tether 32 is pulled away from the protector cap 24, which pulls the protector cap 24 off the femur F and toward the open end 30 of the cannula 22. Separating the protector cap 24 from the femur F could be sufficient to place the protector cap 24 back in the collapsed state, as shown in FIG. 3, or the tether 32 pulling the protector cap 24 against the open end 30 of the cannula 22 with sufficient force could collapse the protector cap 24 back into its collapsed state and into the cannula 22. The connection points' 34, 36 location can be adjusted accordingly to facilitate re-collapsing of the protector cap 24. While two connection points 34 and 36 are shown, there could be only one connection point or more than two connection points, depending on the desired collapsing of the protector cap 24. The tether 32 does not need to be a flexible wire, but could also be a rigid wire or rod.

Optionally, the actuator 26 could also be the tether 32, reducing the number of different parts that are included in the surgical device 10.

Figure 4:
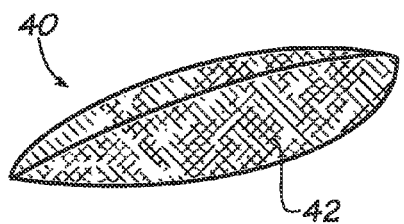
FIG. 4 is a perspective view of an embodiment of the protector cap in a collapsed state.

Referring now to FIG. 4, another embodiment of a protector cap 40 is shown in a collapsed state outside of the guiding instrument 22. As can be seen, the protector cap 40 has a weave pattern made up of fibers 42, which form a fibrous network. While in the collapsed state as shown, the protector cap 40 is able to fit in the guiding instrument 22.

Figure 5:
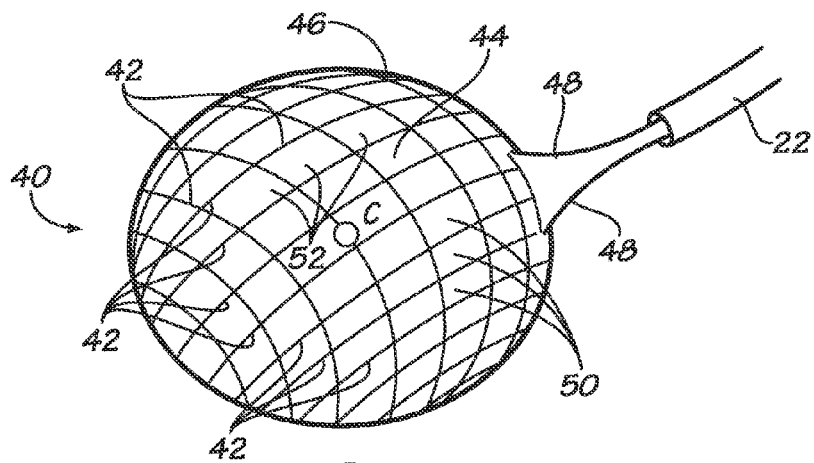
FIG. 5 is a perspective view of the protector cap shown in FIG. 4 in an expanded protection state.

Referring now to FIG. 5, the protector cap 40 is shown in an expanded protection state. In the expanded state, the protector cap 40 has assumed a semi-spherical shape, with the fibers 42 extending along an outer surface 44 of the protector cap 40. The protector cap 40 has a circumference 46, which extends around a center C of the protector cap 40. A spreading wire 48 can be connected to the protector cap 40 and extend around the circumference 46 to assist the protector cap 40 expand when it is advanced out of the guiding instrument 22. The spreading wire 48 can be formed of any material that can help expand the protector cap 40, with shape-memory materials being particularly useful. Shape-memory materials, such as nickel-titanium alloy (Nitinol) or polymers, have shape-memory properties including an original shape and a transformation temperature. The shape-memory material can be plastically deformed into various other shapes at temperatures below the transformation temperature, but will spontaneously attempt to revert to the original shape when heated to or above the transformation temperature. In this respect, shape-memory materials are useful materials for the spreading wire 48 because the shape-memory properties allow the spreading wire 48 to stay in a shape that does not expand the protector cap 40 into the protection state until heated above the transformation temperature, which can be chosen to be slightly below body temperature. Thus, when the protector cap 40 and spreading wire 48 are inserted on to an orthopaedic target that needs to be protected, the protector cap 40 can stay in the collapsed state until the spreading wire 48 has been heated to its transformation temperature, by blood or another heat source, and expands the protector cap 40 into the protection state. In addition to expanding the protector cap 40, the spreading wire 48 can also provide shape rigidity to the protector cap 40 when in its protection state. The spreading wire 48 can also give the ability to collapse the protector cap 40 similarly to the tether 32 previously described and adjust the positioning of the protector cap 40 when expanded by moving the spreading wire 48.

As can be seen in FIG. 5, the protector cap 40 can have relatively large openings 50 formed between the fibers 42 when in the expanded protection state. As previously described, this configuration provides good cutting resistance across the outer surface 44 of the protector cap 40 but can be prone to the point of a sharp surgical instrument going through the openings 50 and damaging the orthopaedic target being covered by the protector cap 40. To reduce this likelihood, a point trapping material 52 can be associated with the fibers 42, by adhesion or otherwise, to reduce the damage caused by the point of a scalpel, needle or other sharp surgical instrument. The point trapping material 52 can be any of the protective materials previously described, including a fibrous network that has very small openings between fibers that do not allow the point to pass through the openings. It is useful if the point trapping material 52 is a silicone or filled silicone material previously described, as the silicone can be soft and trap the point of a surgical instrument within the bulk of the material 52 without transmitting the force to the covered tissue. If a soft material, such as silicone, is used for the point trapping material 52, it is useful if the fibers 42 form the outer surface 44 of the protector cap 40 with the point trapping material 52 attached to an inner surface (toward the center C) of the fibers 42 or the fibers 42 are enveloped and held within the point trapping material 52. Such a configuration allows for the fibers 42 to protect the orthopaedic target from the sharp edge(s) of an instrument and the point trapping material 52 to protect the orthopaedic target from the point of the instrument that might make it through the openings 50 between the fibers. It should be appreciated that by combining fibers 42 that form large openings 50 with a point trapping material 52, a protector cap 40 can be produced that benefits from having good cutting resistance and being less prone to allowing the point of a surgical instrument to pass through to the orthopaedic target.

Figure 6:
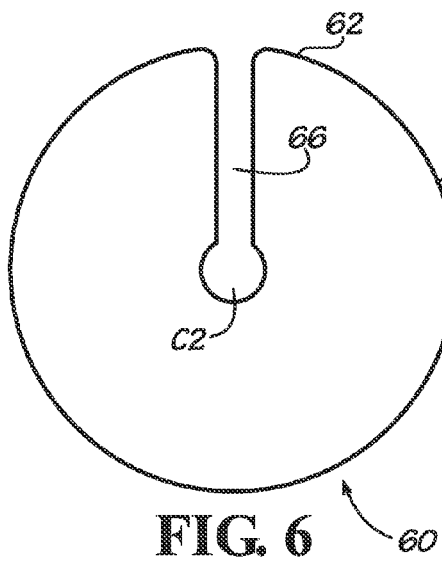
FIG. 6 is a cross-sectional view of another embodiment of a protector cap in an expanded state.
Figure 7:
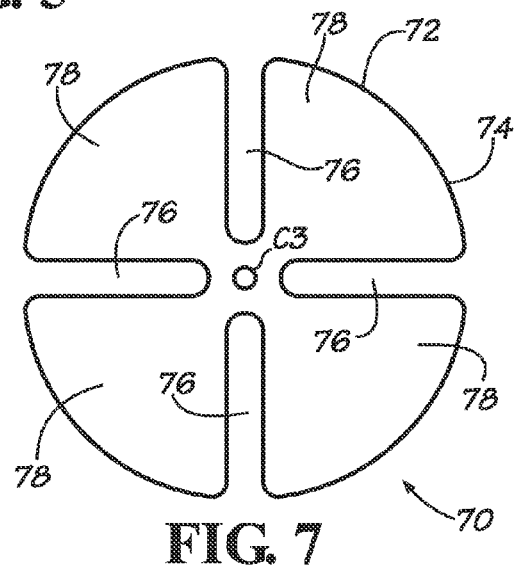
FIG. 7 is a cross-sectional view of yet another embodiment of a protector cap in an expanded state.

Referring now to FIGS. 6 and 7, additional embodiments of protector caps 60, 70 are shown. As can be seen, protector caps 60 and 70 each have a semi-spherical shape with respective edges 62 and 72 that are on circumferences 64 and 74 of the caps 60 and 70. As shown in FIG. 6, a slit 66 extends from and includes center C2 to the edge 62. This slit 66 can help the protector cap 60 to assume the collapsed position more easily and allow for easier adjustment of the protector cap's 60 size. As shown in FIG. 7, the protector cap 70 can also include multiple slits 76 that extend toward center C3 from the edge 72, but do not extend all the way to the center C3. While the four slits 76 are shown as dividing the protector cap 70 into four generally equal sized quadrants 78, the relative positioning of each slit 76 to another slit 76 can be adjusted, as desired, to give different collapsing profiles to the protector cap 70. In this respect, the number of slits formed, how far the slits extend and their location in a protector cap can be varied to adjust the collapsibility of the protector cap and the size that the protector cap will assume in the expanded protection state.

Figure 8:
FIG. 8 is a perspective view of yet another embodiment of a protector cap in an expanded state.

Referring now to FIG. 8, another embodiment of a protector cap 80 is shown that has a semi-spherical shape with an outer surface 82. A pair of protrusions 84 are formed on the outer surface 82 that extend away from the outer surface 82. The protrusions 84 can be shaped as cylinders, as shown, or any other shape that allows for the protrusions 84 to be pushed on. The protrusions 84 can be included on the outer surface 82 to serve a variety of useful purposes. For example, the protrusions 84 can be pushed on by the surgical device 20, guiding instrument 22 or actuator 26 to help position the protector cap 80 on an orthopaedic target or better fixate the protector cap 80 to the orthopaedic target. The protrusions 84 can also be positioned and sized so that they can extend from a femur of a patient to the patient's acetabulum, acting as a spacer between the femur and the acetabulum. Further, a retrieval device (not shown) could be "lassoed" around one or both protrusions 84 to help remove the protector cap 80 after the arthroscopy procedure is finished. In the respect, the protrusions 84 can act as retrieval features, adhesive features and spacing features. The number and size of the protrusions 84 can be adjusted, as desired, to produce a protector cap 80 that meets the specific requirements of a particular arthroscopy procedure. As the protector cap 80 will generally not be implanted in a patient's body for an extended period of time, the protrusions 84 can be, but do not need to be, formed of a material that gives the necessary strength for its given purpose without having to consider long-term biodegradability in the body.

Figure 9:
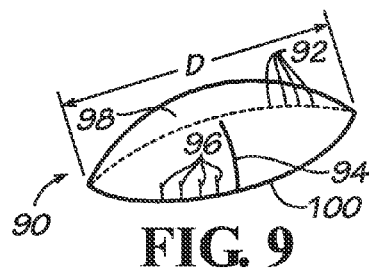
FIG. 9 is a perspective view of yet another embodiment of a protector cap in an expanded state.

Referring now to FIG. 9, another embodiment of a protector cap 90 that has multiple visual indicators 92, 94, 96 is shown in the expanded protection state. The visual indicators 92, 94, 96 can be markings on an outer surface 98 of the protector cap 90, or could be incorporated into the protective material that comprises the protector cap 90. Since the protector cap 90 can be placed on an orthopaedic target early during the arthroscopic procedure, visual indicators 92, 94, 96 on the protector cap 90 can assist the surgeon in determining orientation of surrounding anatomical features relative to the protector cap 90. For example, visual indicator 92, shown as dashed lines going across a diameter D of the protector cap 90, can be imaged by a camera during surgery. Visual indicator 92 could be seen by a surgeon to indicate where the protector cap 90 is, which may not be easily discerned if the protective material is transparent. In this regard, the visual indicator 92 could be a dark dashed line or other indicator that could be easily seen. Visual indicator 94, shown as a dark solid line, could also be included going from visual indicator 92 to an edge 100 of the protector cap 90. Visual indicator 94 in combination with visual indicator 92 could be used by the surgeon to determine the orientation and location of the protector cap 90, and protected orthopaedic target, during the surgery. Visual indicators 96, which are shown as spaced apart marks, could also be included on the outer surface 98. The visual indicators 96 can be spaced apart in a known manner to show measurement of adjacent areas, like a ruler, or could provide a measurement reference when visualized. It should be appreciated that the visual indicators 92, 94, 96 described are exemplary and other visual indicators could be included with the protector cap 90 to serve various useful purposes according to the principles of the present invention.

Figure 10:
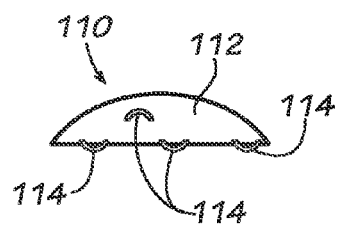
FIG. 10 is a perspective view of yet another embodiment of a protector cap in an expanded state.

Referring now to FIG. 10, another embodiment of a protector cap 110 with an outer surface 112 is shown. Retrieval features 114, shown as loops, are formed on the outer surface 112 that can assist in removing the protector cap 110 from the orthopaedic target following an arthroscopic procedure. A retrieval tool (not shown) could be hooked onto one or more of the loops 114 and pulled so that the protector cap 110 is removed from the orthopaedic target. The spacing and size of the loops 114 can be adjusted, as desired, to provide a protector cap 110 that has one or more retrieval features that can be easily accessed to remove the protector cap 110 following the arthroscopic procedure. Alternatively, the retrieval feature(s) 114 could be formed as holes in the outer surface 112 that can be hooked by a retrieval tool to remove the protector cap 110. Other retrieval features could also be included on the outer surface 112, such as the protrusions 84 previously described, without deviating from the spirit and scope of the present invention.

Figure 11:
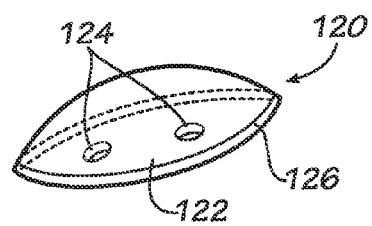
FIG. 11 is a perspective view of yet another embodiment of a protector cap in an expanded state.

Referring now to FIG. 11, another embodiment of a protector cap 120 is shown that has a semi-spherical shape. The protector cap 120 shown has a bottom surface 122 that has adhesive features 124, shown as a pair of suction cups, formed thereon. While a pair of suction cups 124 is shown in FIG. 11 as being on the bottom surface 122, fewer or more suctions cups could be on the bottom surface 122 if desired. The suction cup(s) 124 can be pressed down against an orthopaedic target to provide suction that gives better adhesion of the protector cap 120 to the orthopaedic target. The suction cup(s) 124 can be formed into the bottom surface 122 of the protector cap 120, or could be separate elements that attach to the bottom surface 122. Optionally, rather than a pair of suction cups 124 attached to the bottom surface 122, the entire protector cap 120 could be formed as a single suction cup, such that when the protector cap 120 is pressed down on the orthopaedic target a vacuum will be created between the protector cap 120 and the orthopaedic target that attaches the protector cap 120 to the orthopaedic target. To help release the vacuum caused by the suction cup(s) 124, a lip 126 can be formed on the protector cap 120 that extends out from the protector cap 120 and provides a surface that can be lifted with a retrieval tool (not shown) to release the vacuum that is formed between the suction cup(s) 124 and the orthopaedic target. Once the vacuum is released, the protector cap 120 can be easily removed or adjusted. Optionally, the retrieval tool could press opposing sides of the protector cap 120 towards each other to deform the protector cap 120 in such a way that the vacuum is released. Any other way to release the vacuum formed by the suction cup(s) 124 could also be utilized to adjust or remove the protector cap 120. Although the adhesive features 124 are shown as suction cups, any other type of adhesive feature(s) that can be released from the orthopaedic target could also be incorporated to the protector cap 120. The adhesive features 124 are shown as being on the bottom surface 122, but the adhesive features could also be placed elsewhere on the protector cap 120 to provide a better adhesion of the protector cap 120 to the orthopaedic target.

Figure 12:
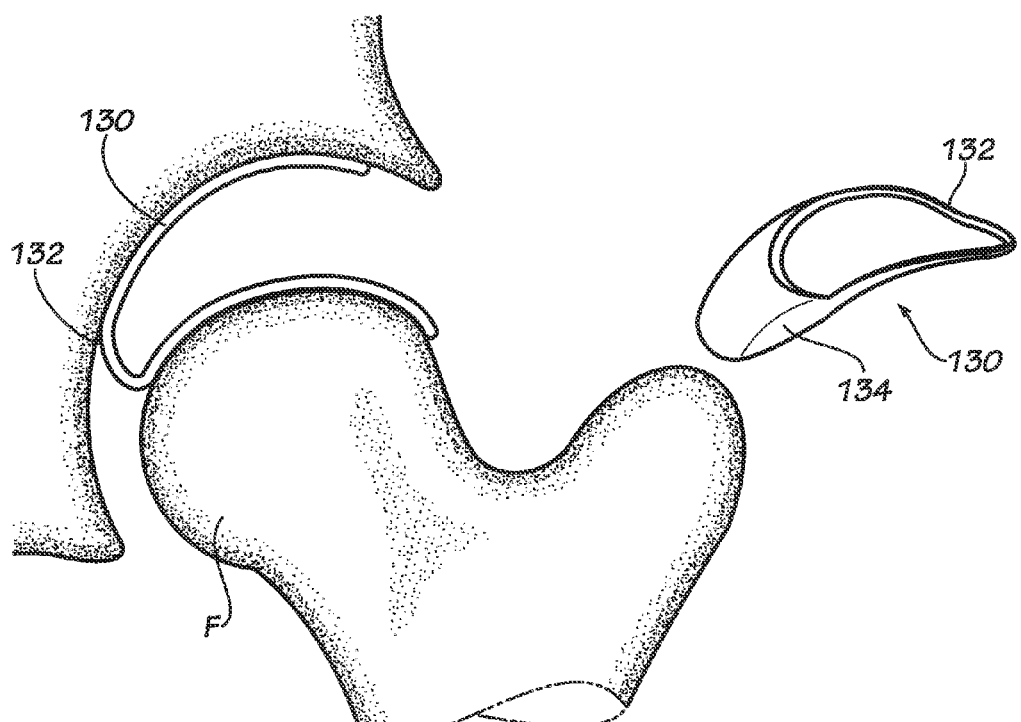
FIG. 12 is a perspective view of yet another embodiment of a protector cap deployed in an expanded protection state on a femur.

Referring now to FIG. 12, another embodiment of a protector cap 130 is shown that has been deployed on a femur F, and more particularly on the femoral head. The protector cap 130 has an elongated base 132 covering an orthopaedic target on the femur F. In certain circumstances, it is desirable to cover more than one orthopaedic target on adjacent anatomical features, such as healthy cartilage on the femur F and an acetabulum. To assist in covering more than one orthopaedic target, the protector cap 130 can have a flap 134 of protective material that attaches to the base 132 and can be pulled away from the base 132 to cover nearby orthopaedic targets. The flap 134 can be formed on the protector cap 130 in any way that allows the flap 134 to extend away from the base 132, such as by folding the protector cap 130 to form the flap 134. When the flap 134 is extended away from the base 132, as shown, the protector cap 130 has more surface area that can protect one or more orthopaedic features.

While protectors that are held on the orthopaedic target during an arthroscopy procedure have been previously described, the present invention also contemplates protectors that are held on a surgical instrument when introducing the instrument near an orthopaedic target to reduce damage to the orthopaedic target.

Figure 13:
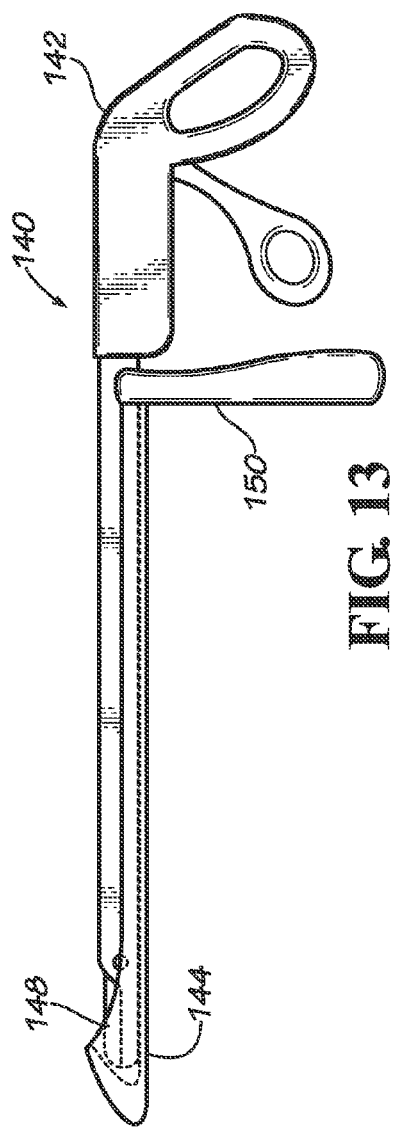
FIG. 13 is a perspective view of another embodiment of a surgical device according to the present invention.
Figure 14:
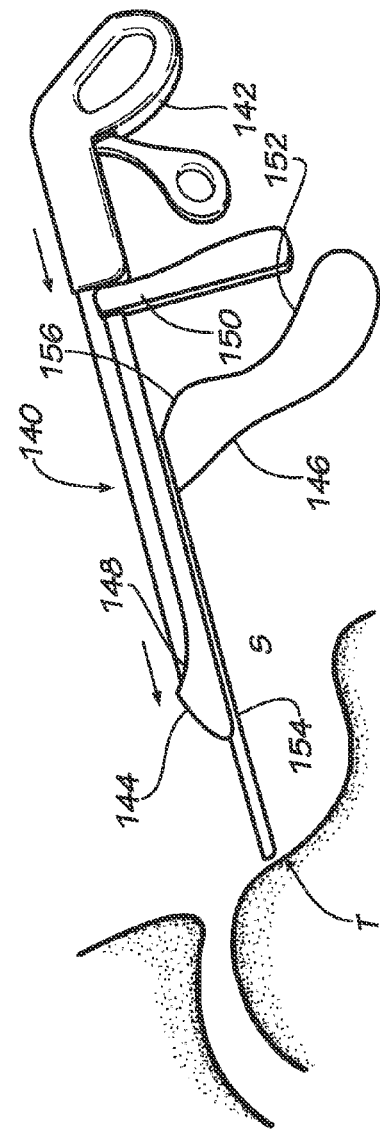
FIG. 14 is a perspective view of a step using the surgical device shown in FIG. 13.
Figure 15:
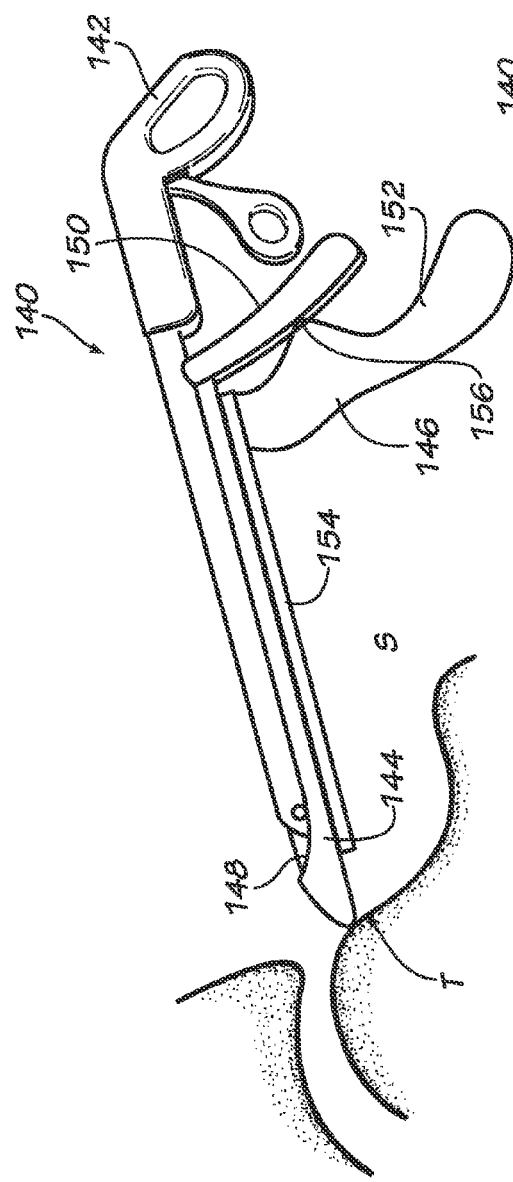
FIG. 15 is a perspective view of a further step using the surgical device shown in FIG. 14.

Referring now to FIGS. 13-16, a surgical device 140 is shown that includes an orthopaedic instrument 142, a protector 144 and a guiding instrument 146 (shown in FIGS. 14 and 15). The orthopaedic instrument 142, shown as a pair of grasping forceps, includes a toothed jaw end 148, which can be referred to as a tissue destructive feature. The tissue destructive feature 148 can be any type of feature that is part of or included with the orthopaedic instrument 142 and specifically designed to engage an anatomical feature in a way that could potentially damage an orthopaedic target through mechanisms such as cutting, tearing, burning, slicing, penetrating, abrading, blunt trauma, etc. The orthopaedic instrument 142 is shown as a pair of grasping forceps, but it is contemplated that the orthopaedic instrument 142 could be any orthopaedic instrument used during surgery such as a scalpel, a suturing needle, etc.

As shown in FIG. 13, a protector 144 is covering the tissue destructive feature 148. The protector 144 can be comprised of any protective material previously described that can reduce the damage that occurs if the orthopaedic instrument 142 is mishandled and the tissue destructive feature 148 improperly engages an orthopaedic target. Such mishandling can include the tissue destructive feature 148 being forced into the orthopaedic target too forcefully or at all. The protector 144 can have an actuator 150 attached that can cause movement of the protector 144 relative to the orthopaedic instrument 142. The actuator 150 can either be formed as a part of the protector 144, as shown, or be a separable element that is connected to the protector 144.

Figure 16:
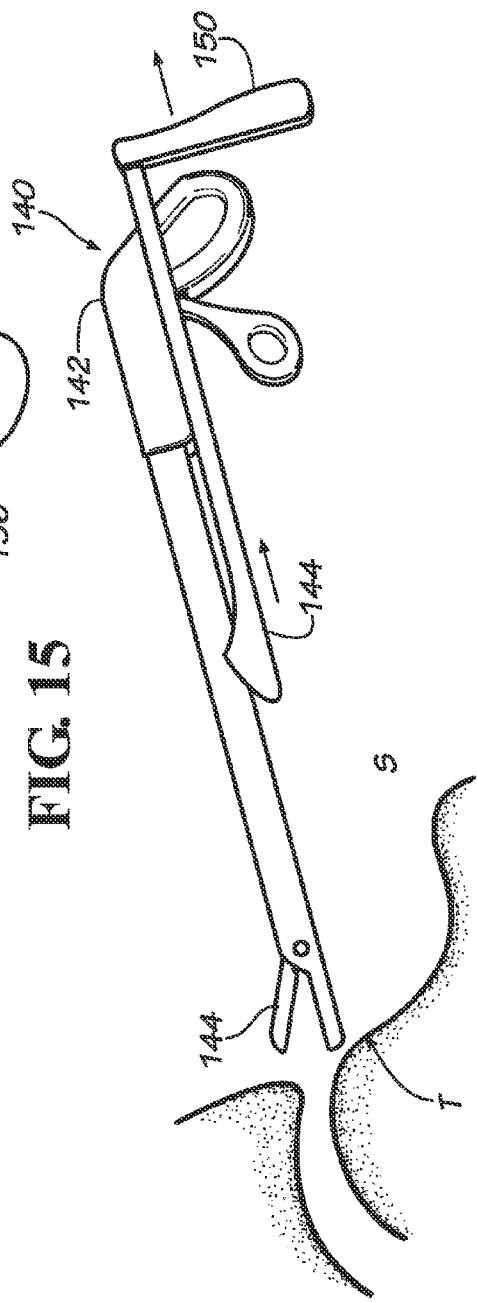
FIG. 16 is a perspective view of a further step using the surgical device shown in FIG. 15.

Referring now to FIG. 14, it can be seen that a guiding instrument 146, shown as an introducer in FIGS. 14-16, has been placed within an anatomical space S and rests adjacent to an orthopaedic target T, shown as a location on a femur. The introducer 146 has a handle portion 152 connected to an elongated portion 154, which has a "half-pipe" shape. The elongated portion 154 provides a guiding pathway for the orthopaedic instrument 142 and protector 144 to reach the orthopaedic target T. The orthopaedic instrument 142 and the protector 144 are placed on the elongated portion 154 with the protector 144 covering the tissue destructive feature 148 and held between the tissue destructive feature 148 and the elongated portion 154. The elongated portion 154 is sized so that the orthopaedic instrument 142 and the protector 144 can slide along a length of the elongated portion 154 toward the orthopaedic target T. At the moment shown in FIG. 14, the orthopaedic instrument 142 and protector 144 are sliding along the introducer 146 in the direction indicated by arrows toward the orthopaedic target T. The protector 144 is in the non-protecting state because the tissue destructive feature 148, if not covered by the protector 144, would be held and mostly covered by the elongated portion 154, which would protect tissue within the anatomical space S.

Referring now to FIG. 15, the orthopaedic instrument 142 and protector 144 have been advanced far enough along the introducer 146 toward the orthopaedic target T that the protector 144 is now in the protection state. As can be seen, the protector 144 is abutted against the orthopaedic target T and preventing the tissue destructive feature 148 from being pressed into the orthopaedic target T, which could potentially damage the orthopaedic target T. In such a case, it is useful if the protector 144 comprises a soft material, such as previously described silicone materials, to reduce the damage that can occur from being pressed into the orthopaedic target T. The orthopaedic instrument 142 and protector 144 are moved along the introducer 146 and adjusted within the anatomical space S until the orthopaedic instrument 142 is in a desired location and orientation. During adjustment of the orthopaedic instrument 142 within the anatomical space S, there is an increased risk of damage to the orthopaedic target T due to the frequent movement of the orthopaedic instrument 142 and associated tissue destructive feature 148. The protector 144 covering the tissue destructive feature 148 can reduce the damage that these frequent movements cause and can be removed once the frequency of the movements and risk of damage to orthopaedic target T are reduced, which is typically when the orthopaedic instrument 142 has the desired location and orientation within the anatomical space S.

Once the orthopaedic instrument 142 is at a desired location and orientation within the anatomical space, the protector 144 can be removed to allow for the tissue destructive feature 148 to be used. To assist in removing the protector 144 from the tissue destructive feature 148, the handle portion 152 can include a stop 156 that is spaced from the elongated portion 154 in such a way that the actuator 150 presses against the stop 156 and prevents further movement of the orthopaedic instrument 142 along the elongated portion 154. In this configuration, the actuator 150, which is a part of the protector 144, can be flexible and pushed toward the orthopaedic target T while the orthopaedic instrument 142 is held in place. The flexible actuator 150 can then deform from the pushing and push the protector 144 a farther distance along the elongated portion 154 than the orthopaedic instrument 142 and associated tissue destructive feature 148, sliding the protector 144 off of the tissue destructive feature 148. Once the protector 144 slides off the tissue destructive feature 148, the introducer 146 can be removed from the anatomical space S, leaving the orthopaedic instrument 142 and protector 144 within the anatomical space S and free to move. As shown in FIG. 16, the protector 144 can then be removed from the anatomical space S by pulling the protector 144 out of the anatomical space S, leaving the orthopaedic instrument 142 and associated tissue destructive feature 148 at a desired location and orientation within the anatomical space S that is past the orthopaedic target T. It should be appreciated that the protector 144 can be altered in different ways to protect an orthopaedic target from different tissue destructive features 148 on a variety of orthopaedic instruments 142. Similarly, it should be appreciated that the protector 144 can switch between the non-protecting and protection states by a variety of different mechanisms, so long as the switch can occur when the protector 144 is advanced along a guiding instrument in such a way that the protector 144 can reduce the potential trauma that an orthopaedic target may experience during an arthroscopic procedure.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical device, comprising:
   an orthopaedic instrument having a tissue destructive feature;
   a guiding instrument configured to be connected to said orthopaedic instrument;
   a protector comprised of a protective material held in a collapsed non-protecting state by said guiding instrument, said protector having an expanded protection state, said protector configured for protecting an orthopaedic target from the tissue destructive feature when in the expanded protection state;
   an actuator connected to said protector, said actuator configured to advance said protector along said guiding instrument such that said protector is allowed to assume said expanded protection state; and
   a tether held by said guiding instrument and connected to said protector, said tether formed as a wire, said tether configured to collapse said protector from said expanded protection state when pulled away from said protector.

2. The surgical device according to claim 1, wherein said protector is configured to self-expand into said expanded protection state outside of said guiding instrument.

3. The surgical device according to claim 1, wherein said actuator is configured to expand said protector into said expanded protection state outside of said guiding instrument.

4. The surgical device according to claim 1, wherein said protector includes a spreading wire configured to deploy said protector into said expanded protection state.

5. The surgical device according to claim 4, wherein said spreading wire comprises a shape-memory material.

6. The surgical device according to claim 1, wherein said guiding instrument is at least one of a cannula and an introducer.

7. The surgical device according to claim 1, wherein said protective material comprises at least one of a silicone material, a filled silicone material, a fiber reinforced silicone material, an ultra-high molecular weight polyethylene (UEMWPE) fiber, a polyester, a polypropylene, a nylon, layered carbon material and thermoplastic.

8. The surgical device according to claim 1, wherein said protector includes a fibrous network incorporated into said protective material.

9. The surgical device according to claim 1, wherein said protector has an outer surface that includes at least one of a retrieval feature, an adhesive feature and a spacing feature formed thereon.

10. The surgical device according to claim 1, wherein said protective material is one of translucent and transparent.

11. The surgical device according to claim 1, wherein said protector includes at least one visual indicator.

12. The surgical device according to claim 1, wherein said protector has an edge and at least one slit that extends to said edge.

13. The surgical device according to claim 1, wherein said protector has a base and a protector flap connected to said base that is configured to extend away from said base.

14. A surgical device, comprising:
an orthopaedic instrument having a tissue destructive feature;
a guiding instrument connected to said orthopaedic instrument, said guiding instrument configured to allow said orthopaedic instrument to slide along said guiding instrument;
a protector comprised of a protective material covering said tissue destructive feature and held by said guiding instrument, said protector configured to be releasably attached to said tissue destructive feature, said protector configured to slide farther along said guiding instrument than said tissue destructive feature and release from said tissue destructive feature after sliding a farther distance along said guiding instrument than said tissue destructive feature; and
a tether held by said guiding instrument and connected to said protector, said tether formed as a wire, said tether configured to collapse said protector from an expanded protection state when pulled away from said protector.

* * * * *

UNITED STATES PATENT AND TRADEMARK OFFICE
CERTIFICATE OF CORRECTION

PATENT NO. : 9,801,692 B2
APPLICATION NO. : 14/454007
DATED : October 31, 2017
INVENTOR(S) : White et al.

It is certified that error appears in the above-identified patent and that said Letters Patent is hereby corrected as shown below:

In the Claims

In Column 11, Line 14, in Claim 7, delete "(UEMWPE)" and insert --(UHMWPE)-- therefor Signed and Sealed this
Twenty-seventh Day of March, 2018

Andrei Iancu
*Director of the United States Patent and Trademark Office*